United States Patent [19]

Arai et al.

[11] Patent Number: 4,783,315
[45] Date of Patent: Nov. 8, 1988

[54] ANALYSIS MATERIAL SHEET

[75] Inventors: Fuminori Arai; Kenichiro Yazawa; Hideaki Takeuchi; Masao Kitajima, all of Saitama, Japan

[73] Assignee: Fuji Photo Film Co., Ltd., Kanagawa, Japan

[21] Appl. No.: 758,562

[22] Filed: Jul. 23, 1985

Related U.S. Application Data

[63] Continuation of Ser. No. 554,655, Nov. 23, 1983, abandoned, which is a continuation of Ser. No. 310,257, Oct. 9, 1981, abandoned.

[30] Foreign Application Priority Data

Oct. 9, 1980 [JP] Japan ................... 55-140532

[51] Int. Cl.$^4$ ............................................. G01N 31/22
[52] U.S. Cl. .................................. 422/56; 428/475.2; 428/476.3; 422/57
[58] Field of Search ......................... 422/55–58; 436/169, 170; 435/805; 428/475.2, 476.3

[56] References Cited

U.S. PATENT DOCUMENTS

| | | | |
|---|---|---|---|
| 3,874,877 | 4/1975 | Omichi et al. | 428/475.2 X |
| 3,897,214 | 7/1975 | Lange et al. | 422/56 |
| 3,944,709 | 3/1976 | Levy | 428/475.2 X |
| 3,950,206 | 4/1976 | Adachi et al. | 428/475.2 X |
| 4,233,029 | 11/1980 | Columbus | 422/58 X |
| 4,292,272 | 9/1981 | Kitajima et al. | 422/56 X |

*Primary Examiner*—Michael S. Marcus
*Attorney, Agent, or Firm*—Sughrue, Mion, Zinn, Macpeak & Seas

[57] ABSTRACT

An analysis material sheet is disclosed which is comprised of layers of material with strong adhesion for one another. The sheet includes a water-impermeable support having provided directly or indirectly thereon a layer of fabric. The fabric contains a hydrophobic organic polymer fiber and is physically activated on at least one surface thereof, with the physically activated surface being adhered directly or indirectly to the support. A reagent layer can be provided directly or indirectly on the liquid sample-spreading layer of fabric. By utilizing a fabric containing a hydrophobic organic polymer fiber, body fluids to be analyzed can be quickly and uniformly spread and by utilizing the physically activated surface of the fabric, strong adhesion between the layers can be obtained.

22 Claims, 2 Drawing Sheets

ANALYSIS MATERIAL SHEET

This is a continuation of application Ser. No. 554,655, filed Nov. 23, 1985, which is a continuation of application Ser. No. 310,257, filed Oct. 9, 1981, both now abandoned.

FIELD OF THE INVENTION

This invention relates to a liquid sample analysis material sheet comprising a layer composed of a fabric containing a hydrophobic organic polymer fiber which is rendered hydrophilic on at least one surface thereof by a physically activating treatment, and to a multilayered, liquid sample analysis material sheet comprising at least a sample-spreading layer composed of the fabric treated as described above and a reagent layer.

BACKGROUND OF THE INVENTION

Filter paper form analysis sheets or multilayered analysis sheets are known as useful material for rapid, simple, dry process semi-quantitative or quantitative analysis of specific chemical components contained in an aqueous liquid such as body fluid (e.g., blood, serum, urine or spinal fluid). Multilayered analysis sheets are described in detail in, for example, Japanese patent application (OPI) No. 53888/74 (U.S. Pat. No. 3,992,158), U.S. Pat. No. 3,992,158, Japanese patent application (OPI) Nos. 137192/75 (U.S. Pat. No. 3,983,005), 40191/76 (U.S. Pat. No. 4,042,335), 3488/77 (U.S. Pat. No. Re. 30,267), 131786/77 (U.S. Pat. No. 4,050,898), 131089/78 (U.S. Pat. No. 4,144,306), 29700/79 (U.S. Pat. No. 4,166,093), 34298/79 (U.S. patent application Ser. No. 814,770, filed July 11, 1977), 90859/80 (U.S. Pat. No. 4,258,001), U.S. Pat. Nos. 4,110,079, 4,132,528 (the term "OPI" as used herein refers to a "published unexamined Japanese patent application"), and *Clinical Chemistry*, Vol. 24, pp. 1335–1350 (1978), etc. Such multilayered analysis sheets are comprised of a support having previously laminated thereon a liquid sample-spreading layer and a reagent layer containing reagents necessary for the intended analysis. In practicing chemical analysis, quantitative analysis can only be conducted by two fundamental procedures of applying a drop of test sample onto the sheet and measuring color change in terms of optical denesity. Thus, they are dry-process chemical analysis materials which do not require use of test tubes, preparation, weighing and addition of reagent solutions, and strict weighing-out of samples; as distinct from conventional analytical methods.

The fundamental structure of such multilayered chemical analysis sheet includes a support, a reagent layer, and a sample-spreading layer in that order. The reagent layer is formed by incorporating a reagent in a binder, such as gelatin, and forming it into a thin layer. The reagent layer may be a single layer, separated into different layers such as a first reagent layer and a second reagent layer, or may contain additional layers such as detection layers, or dye-receiving layers. In addition, an interlayer called a color- (radiation-) blocking layer or a barrier layer may be provided between the spreading layer and the reagent layer or between a plurality of reagent layers. The sample-spreading layer is provided as an outermost layer of the analysis sheet, to which a liquid sample is to be applied. The sample-spreading layer functions to transport the liquid sample in an almost definite quantity per unit area to the reagent layer regardless the volume of the applied liquid sample, i.e., functions to substantially uniformly spread the sample.

The liquid sample-spreading layer as described above is decribed in detail in the aforesaid patent specifications and literature. These descriptions indicate that non-fibrous porous media are effective as such sample-spreading layer.

Examples of such non-fibrous porous media include brush polymer (general name: membrane filter) and a dispersion of a porous material such as diatomaceous earth or a fine crystalline material (e.g., fine crystalline cellulose (trade name: Avicel, made by FMC Corp.), etc.) in a binder, porous joining material made by point-to-point adhesion of glass or resin fine spherical beads (see U.S. Pat. No. 4,258,001). The non-fibrous porous media illustrated must contain voids uniformly positioned in every direction or have an isotropic porosity as clearly described in U.S. Pat. No. 3,992,158.

Japanese patent application (OPI) Nos. 53888/74 and 90859/80 and U.S. Pat. No. 3,992,158 disclose in detail the process for forming the liquid sample-spreading layer composed of a non-fibrous, isotropically porous medium. However, a known sample-spreading layer composed of a non-fibrous porous medium is undesirable because when a sample applied to it contains protein in a high concentration (e.g., blood serum), the ability of the layer to spread the applied liquid sample varies substantially depending upon the content of the protein. Accordingly, the quantitative aspect of the analysis is spoiled.

When the non-fibrous porous medium is a structure comprising self-adhesive particles, heat- or solvent-softened particles are liable to readily fix and fill voids within the structure. Accordingly, many high molecular weight materials present in an aqueous liquid sample to be analyzed result in readily stuffing and therefore inhibit the fluid flow within the structure. When the structure is composed of particles bound to each other through an adhesive, stuffing also can take place due to the volume of the adhesive, thus inhibiting the flow of a fluid containing composite high molecular weight materials.

Therefore, multilayered chemical analysis materials containing such non-fibrous porous medium as a liquid sample-spreading layer are not suited for analysis of body fluid containing macro-molecules or whole blood containing erythrocytes.

One approach for removing the defects described above with known non-fibrous porous medium-containing liquid sample-spreading layer is described in Japanese patent application (OPI) No. 90859/80. The present inventors have formerly proposed to use fabric rendered hydrophilic as a liquid sample-spreading layer for a multilayered chemical analysis material (U.S. Pat. No. 4,292,272) as an art absolutely different from that disclosed in Japanese patent application (OPI) No. 90859/80. The spreading layer using such a fabric rendered hydrophilic removes defects of known non-fibrous porous media with respect to ease and stability of production steps, production cost, and sample-spreading properties.

The multilayered chemical analysis sheet having a spreading layer of fabric rendered hydrophilic is excellent to enable one to use the whole blood upon quantitative analysis of blood component. However, it still has several problems.

When preparing a spreading layer from natural fiber such as 100% cotton, it is difficult to attain uniform spreading of an applied liquid sample as compared to a fabric containing a chemical or synthetic fiber due to non-uniformity in the yarn structure, particularly in disposition or weaving manner of twisted yarns. Furthermore, a spreading layer composed of natural fiber alone is difficult to handle due to its strong water-absorbing properties, generally high water content, and high stretchability. In addition, with respect to the whole blood-spreading properties, the layer composed of a natural fiber is inferior to that composed of a fabric containing a chemical or synthetic fiber. On the other hand, a sample-spreading layer composed of a fabric containing a chemical or synthetic fiber makes it possible to attain uniform spreading of an applied liquid sample due to uniformity in yarn structure, particularly in disposition and weaving manner of twisted yarns. A chemical or synthetic fiber is easy to handle due to weak or substantially no water-absorbing properties and small stretchability. Further, such a spreading layer composed of a fabric containing a chemical or synthetic fiber has an excellent whole blood-spreading ability. However, it has such poor adhesiveness that it is easily delaminated when subjected to cutting or punching work.

As a result of intensive investigations to remove the defects with such spreading layers composed of fabrics containing chemical or synthetic fibers, the inventors have achieved the present invention.

SUMMARY OF THE INVENTION

An object of the present invention is to provide an analysis material sheet comprising a layer composed of a fabric containing a hydrophobic organic polymer fiber physically activated on at least one surface.

Another object of the present invention is to provide a multilayered chemical analysis material sheet comprising at least a sample-spreading layer composed of such a fiber and a reagent layer.

Still another object is to provide an analysis material sheet comprising a water-impermeable support having provided directly or indirectly thereon a layer of fabric, the fabric containing a hydrophobic organic polymer fiber and being physically activated on at least one surface thereof, with the physically activated surface being adhered directly or indirectly to the support, to thereby form an integral structure.

Further object is to provide an analysis material sheet comprising at least one reagent layer having provided directly or indirectly thereon a liquid sample-spreading layer of fabric, the fabric containing a hydrophobic organic polymer fiber and being physically activated on at least one surface thereof, with the physically activated surface being adhered directly or indirectly to the reagent layer, to thereby form an integral structure.

Still further object is to provide an analysis material sheet comprising at least one reagent layer having provided directly or indirectly thereon a liquid sample-spreading layer of fabric, the fabric containing a hydrophobic organic polymer fiber and being physically activated on at least one surface thereof, with the physically activated surface being adhered directly or indirectly to the reagent layer, to thereby form an integral structure, wherein the reagent layer is water-permeable, and a light-transmitting and water-impermeable support is provided on a side opposite the spreading layer.

DETAILED DESCRIPTION OF THE INVENTION

Figure 1:
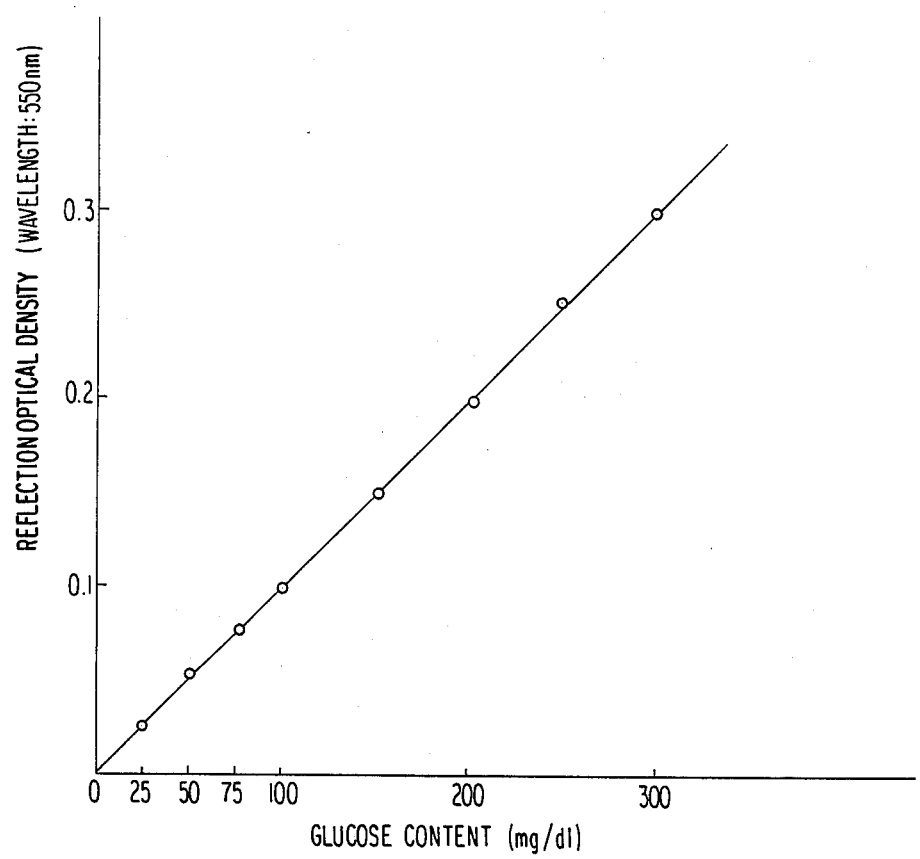
FIG. 1 is a graph showing the relationship between glucose content in control serum and reflection optical density using a multilayered analysis sheet as obtained from Example 1.

In coating or laminating a layer on a plastic film having a small surface energy such as polyethylene, polypropylene, or polyethylene terephthalate, the films are often previously subjected to surface treatments which raise the surface energy or render the surface polar, thus adhesion force between such and a coating or lamina is improved. Of such surface treatments, those of conducting surface oxidation through physical means, such as glow discharge treatment, plasma discharge treatment, UV light irradiation treatment, corona discharge treatment, flame treatment, etc., are well known.

The present invention is based on the finding that the adhesiveness of a fabric containing a hydrophobic organic polymer fiber can be improved by applying such known surface-oxidizing methods for plastic films by physical means to at least one surface thereof.

The fabrics containing hydrophobic organic polymer fibers to be used in the present invention mean those of single or mixed chemical or synthetic fibers such as cellulose acetate, cellulose triacetate, polyvinyl alcohol series polymers (e.g., vinylon), polyesters (e.g., polyethylene terephthalate, polyethylene terephthlate isophthalate, polyethylene terephthalate p-hydroxybenzoate, etc.), polyamides (e.g., nylon-6, nylon-6,10, nylon-11, etc.), polyacrylonitrile; or mixtures or mixed yarns of such chemical or synthetic fibers and natural fibers (e.g., cotton, kapok, flax, hemp, ramie, silk, etc.). Different fabric structures may be used, however. Plain weaves formed by warp and weft are preferred. Where mixed yarns of chemical or synthetic fiber and natural fiber are employed, the mixing degree is not particularly limited, but those having an amount of chemical or synthetic fiber of about 10% or more, preferably about 30% or more, are generally used, with fabric of mixed yarns comprising 65% of polyethylene terephthalate and 35% of cotton being advantageous in view of availability.

The above-described fabrics may be rendered adhesive or improved with respect to adhesiveness by subjecting at least one surface to a physical activating treatment such as a glow discharge treatment, plasma discharge treatment, UV light irradiation treatment, corona discharge treatment or flame treatment. Such a physical activating treatment may be subjected to on both surfaces. The details of glow discharge treatment, plasma discharge treatment, UV light irradiation treatment, corona discharge treatment, flame treatment, etc., are known to those skilled in the art and can be applied as such. Fabric treated in this manner, having an adhesive force ranging from about 10 to about 1,000 g/cm, preferably from about 20 to about 500 g/cm (measured by a Tensilon) can be used.

Fabric treated by one of these treatments is then laminated directly or indirectly on a support to produce a chemical analysis material sheet. In this case, a reagent or reagents for quantitative analysis of a specific chemical component in an aqueous liquid sample and various auxiliary agents are impregnated into the fabric either before or after the lamination of the fabric on the support.

The fabric can also be intimately laminated as a spreading layer on a reagent layer containing at least a reagent for quantitative analysis of a specific chemical component in an aqueous liquid sample to produce a multilayered chemical analysis material sheet.

When a mixed yarn of chemical or synthetic fiber and natural fiber is used as a liquid sample-spreading layer, by the physical oxidation treatment, not only the adhesion of this layer to a sheet containing a reagent layer increases but also an ability for uniformly spreading whole blood that the mixed yarn originally possesses is markedly improved.

Examples of useful supports include water-impermeable transparent supports having a thickness of about 50 $\mu$m to about 2 mm such as films of polyethylene terephthalate, cellulose esters (e.g., cellulose diacetate, cellulose triacetate, cellulose acetate propionate, etc.), polycarbonate and polymethyl methacrylate.

The reagent layer is formed by applying in a thickness of about 1 $\mu$m to about 100 $\mu$m a composition containing a reagent for quantitative analysis of a specific component in a liquid sample (aqueous liquid sample in this specification) dispersed in a known hydrophilic binder. Examples of useful binders include gelatin, polyvinyl alcohol, polyvinylpyrrolidone, agarose and sodium polyvinylbenzenesulfonate. For example, a reagent layer for quantitative analysis of glucose in a liquid sample is formed in a thickness of about 10 $\mu$m to about 20 $\mu$m by coating a composition primarily containing the four ingredients of glucose oxidase, peroxidase, aminoantipyrine and 1,7-dihydroxynaphthalene using gelatin as a binder.

In preparing a multilayered chemical analysis material sheet comprising a reagent layer and a spreading layer, a liquid sample-spreading layer comprising the fabric having been treated as described above can be provided directly adjacent the reagent layer adhered onto the support as necessary. It may also be desirable to provide an analytical function auxiliary layer such as a color- (or radiation-)blocking layer or a light-reflecting layer on the reagent layer and to laminate the liquid sample-spreading layer comprising fabric on the reagent layer. When providing an analytical function auxiliary layer such as a color- (or radiation-)blocking layer or a light-reflecting layer on the reagent layer, there may be further provided a structural auxiliary layer such as an adhesive layer having laminated thereon a liquid sample-spreading layer comprising fabric. When providing a structural auxiliary layer such as an adhesive layer on the reagent layer, the liquid sample-spreading layer comprising fabric may be laminated thereon.

The color- (or radiation-)blocking layer is useful for quantitative analysis of colored particle-containing liquid samples such as the whole blood containing erythrocytes. The color of the colored particles behind the color- (or radiation-)blocking layer is blocked by the color- (or radiation-)blocking layer, and the color of the colored particles is not seen from the opposite side. Accordingly, the colored particles do not inhibit quantitative analysis carried out by means of colorimetry. The color- (or radiation-)blocking layer is a layer of fine powder such as titanium dioxide fine powder, barium sulfate fine powder or aluminum fine powder dispersed in a water-permeable hydrophilic polymer binder having a thickness of about 5 $\mu$m to about 100 $\mu$m, preferably about 5 $\mu$m to about 30 $\mu$m, through which a liquid sample can permeate.

The liquid sample-spreading layer of the present invention may contain all or all of reagents necessary for analysis.

Where an adhesive layer is provided as a structural auxiliary layer, it functions mainly to strengthen adhesion between the reagent layer or the analytical function auxiliary layer such as the color- (or radiation-)blocking layer or the light-reflecting layer and the liquid sample-spreading layer comprising fabric. Examples of materials used in the adhesive layer include hydrophilic polymers used as binders for the reagent layer or the analytical function auxiliary layer (such as the color- (or radiation-)blocking layer or the light-reflecting layer). The liquid sample-spreading layer comprising fabric can be adhered onto the adhesive layer by pressing, with a suitable pressure, the sample-spreading layer onto the adhesive layer while the hydrophilic polymer of the adhesive layer is in a semi-dried state or while the hydrophilic polymer layer is moistened with water, or water containing a surfactant. The thickness of the adhesive layer ranges from about 0.5 $\mu$m to about 15 $\mu$m, preferably from about 0.5 $\mu$m to about 5 $\mu$m.

The thus-obtained analysis material sheet, chemical analysis material sheet, or multilayered chemical analysis material sheet does not undergo film delamination (delamination of the sample-spreading layer comprising fabric from the support, reagent layer, structural auxiliary layer, or analytical function auxiliary layer) even when subjecteed to cutting or punching work due to strong adhesion between respective layers.

The analysis material sheet or the multilayered chemical analysis material sheet of the present invention is convenient for quantitative analysis of a specific component in an aqueous liquid. It is particularly suited for quantitative analysis of, for example, glucose, urea, bilirubin, cholesterol, protein, or enzyme in body fluids such as urine or blood. With a blood sample, a specific component in blood can be determined without being seriously influenced by the contents of components contained therein whether the sample is serum or whole blood. This is a great advantage of the analysis material of the present invention.

The present invention is now described in more detail by reference to the examples which, however, are not to be construed as limiting the present invention in any way.

EXAMPLE 1

A 185-$\mu$m thick colorless transparent polyethylene terephthlate film subjected to an undercoating treatment for a gelatin layer was coated with a reagent layer for quantitative analysis of glucose having the following formulation in a dry thickness of about 15 μm.

|  | parts by weight |
|---|---|
| Glucose oxidase | 2 |
| Peroxidase | 1 |
| 1,7-Dihydroxyhaphthalene | 5 |
| 4-Aminoantipyrine | 5 |
| Alkali-processed gelatin | 200 |
| Nonion HS 210 (nonionic surfactant, trade name for polyoxyethylene nonylphenyl ether, made by Nippon Oils & Fats Co., Ltd.) | 2 |

On this reagent layer was coated a color- (or radiation-)blocking layer in a dry thickness of about 15 μm using an aqueous dispersion of a mixture of gelatin and titanium dioxide fine powder (1:8 by weight in a dry state). Further, an adhesive layer comprising gelatin containing 0.2% of a nonionic surfactant (Nonion HS 210) was coated thereon in a dry thickness of about 5 μm.

One side of a cotton broad cloth woven by mixed cotton yarns of 80 counts (65% of KSR 808000 made by Kurabo Co., Ltd. using a Tetron (trade name for polyethylene terephthalate made by Toray Industries, Inc.) and 35% of cotton) was subjected to a glow discharge treatment for 60 seconds (while properly controlling pressure so as to realize the conditions of 50 Hz, 600 V, 0.5 A) to prepare a fabric for a liquid sample-spreading layer.

The formerly prepared glucose analysis sheet was substantially uniformly moistened with a 0.2% nonionic surfactant (Nonion HS 210) aqueous solution, and the above-described fabric for liquid sample-spreading layer was immediately brought into intimate contact with the moistened sheet with the side of the fabric nearer the electrode in the glow discharge treatment facing the quantitative analysis sheeet for glucose. The resulting assembly was then passed between pressing rollers to uniformly laminate the two layers on each other. The thus-obtained laminate showed strong adhesion after being dried. The adhesion force of the laminated spreading layer was measured to be 100 g/cm by means of a Tensilon. Thus, a multilayered analysis sheet for quantitative analysis of glucose was obtained.

This multilayered analysis sheet was punched into 2×2 cm pieces using a precision bench press, BPN-100S (made by Nippon Automatic Machine K.K.), to prepare analysis pieces. During this process no delamination of the spreading layer occurred.

The thus-obtained multilayered analysis pieces for quantitative analysis of glucose were mounted on slide frames to prepare chemical analysis slides for quantitative analysis of glucose.

A 6 μl control serum sample containing 7% of bovine albumin and 100 mg/dl of glucose was applied to the spreading layer of this slide. Spreading of the sample was completed in about 1 second, with the control serum being spread in a circle of about 10 mm in diameter. When this analysis slide was incubated for 10 minutes in a 37° C. thermostatic chamber, substantially uniformly colored circle having a maximum absorption wavelength of 495 nm was formed in the reagent layer.

The reflection optical density of the colored circle was measured at the central portion thereof using a Macbeth reflection densitometer RD504 (maximum transmission wavelength: 550 nm).

Control serums containing glucose in varying concentrations of about 25, 50, 75, 100, 150, 200, 250, and 300 mg/dl were prepared in the same manner as described above, and 6 μl portions of respective control serums were applied to the analysis slides to measure the color density according to the method described above. The glucose concentration in the control serum samples and the reflection optical density of colored circles formed (determined by subtracting fog optical density) were found to have a linear relation with each other as shown in FIG. 1.

EXAMPLE 2

Following procedures described in Example 1 except for changing the glow discharge treatment conditions to 60 sec, 50 Hz, 1,000 V, and 0.6 A, a fabric for a liquid sample-spreading layer was prepared.

This fabric was laminated on the analysis sheet for glucose prepared as in Example 1 to obtain a quantitative analysis sheet. The spreading layer had an adhesion force of 150 g/cm. The quantitative analysis sheet was cut into 2×2 cm multilayered analysis pieces for quantitative analysis of glucose using a bench press without any difficulties, such as delamination. The resulting analysis pieces were placed in slide frames to prepare chemical analysis slides.

A 10 μl fresh blood sample (containing heparin) collected from a healthy human was applied to the liquid sample-spreading layer comprising fabric in the chemical analysis slide. The applied blood sample was spread rapidly and uniformly as with the control serum, and the spreading was completed in about 2 seconds, with the blood being spread in a circle of about 10 mm in diameter. Incubation was conducted at 37° C. for 10 seconds.

Figure 2:
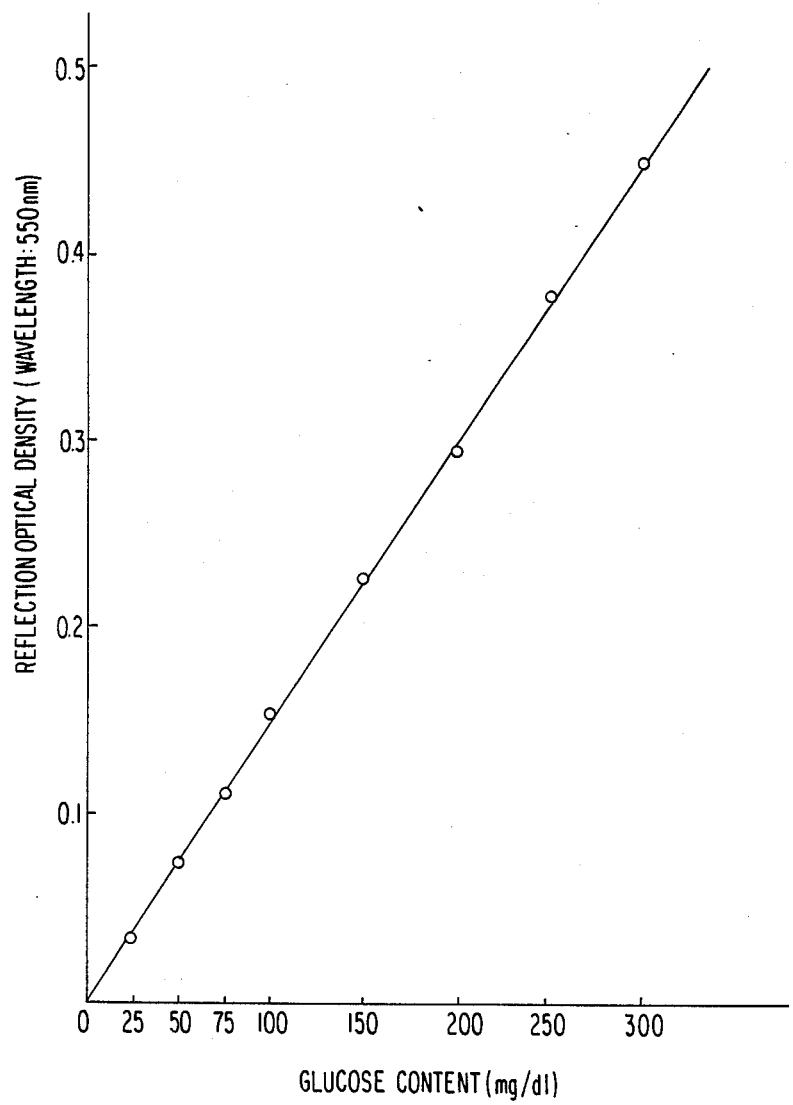
FIG. 2 is a graph showing the relationship between glucose content in control serum and reflection optical density using the multilayered analysis sheet as obtained in Example 2.

Control bloods containing glucose in varying concentrations of about 50, 100, 150, 200, 250 and 300 mg/dl were prepared, and 10 μl portions of the respective control blood samples were applied to the analysis pieces. Thereafter, the color density was measured using a Macbeth reflection densitometer, RD504. As a result, the glucose concentration in the control blood samples and the reflection optical density (determined by subtracting fog optical density) were found to have a linear relationship with each other as shown in FIG. 2.

COMPARATIVE EXAMPLE 1

The same cotton broad cloth as used in Example 1 was laminated, without the glow discharge treatment, on the formerly prepared analysis sheet for glucose in the same manner as in Example 1.

The spreading layer of the thus-prepared laminate had an adhesion force of 10 g/cm. When this quantitative analysis sheet was punched as in Example 1, the spreading layer was delaminated. Thus, the sheet was found to possess no workability. However, careful cutting with scissors produced analysis pieces. In this case, the glucose-analyzing ability was found to be about the same as in Example 1.

EXAMPLE 3

One side of 100-count mixed yarn cotton broad cloth (polyester (polyethylene terephthalate made by Toray Industries, Inc.): cotton=65:35, trade name: Kurabo KSR 90900) was subjected to a glow discharge treatment. The glow discharge conditions and the adhesion force of the thus-treated surface for gelatin membrane are as shown in Table 1.

TABLE 1

| Treating Time (sec) | Electric Power | |
|---|---|---|
| | 300 W (600 V A.C., 0.5 A) | 600 W (1,000 V A.C., 0.6 A) |
| 60 | 85 ± 15 g/cm | 150 ± 25 g/cm |
| 30 | 45 ± 15 | 100 ± 15 |
| 15 | 15 | 25 ± 10 |
| 6 | 10 | 10 |
| No treatment | 10 | 10 |

The adhesion force was measured as follows.

Gelatin was coated on a glass plate in a thickness of 35 g/m² and dried. A 2-cm cotton broad cloth moistened with water was pressed thereonto and dried. The force necessary for delaminating the cloth from the gelatin surface was measured using a Tensilon (UTM-IIILH) made by Toyo Hybrid K.K.

EXAMPLE 4

Following procedures described in Example 1 except for using 100-count mixed yarn cotton broad cloth [polyester (polyethylene terephthlate (made by Teijin Limited)): cotton=66:35, made by Nisshin Cotton Spinning Co., Ltd., product No. T1000], the same results as in Example 1 were obtained.

EXAMPLE 5 AND COMPARATIVE EXAMPLE 2

Using respective 100% cotton broad cloth (80 yarn counts; made by Toyo Spinning Co., Ltd.) and the cotton broad cloth woven by mixed cotton yarns (80 yarn counts) as used in Example 1 as a liquid sample-spreading layer, multilayered analysis sheets for quantitative analysis of glucose were prepared in the same manner as in Example 1.

A 2 ml fresh blood taken from a healthy human vein was drawn into a test tube in which 40 units of heparin and 6 mg of NaF had been contained, and mildly stirred and shaken. After intimately mixing, the blood was lightly subjected to centrifugal treatment whereby a concentrated erythrocyte portion and a blood plasma portion were separated. Thereafter, both were mixed with each other with various volume ratios to form blood samples having various hematocrit values.

When a whole blood sample having a hematocrit value (HCT) of 31% was applied to the multilayered analysis sheet comprising a spreading layer of 100% cotton, the sample was slowly spread uniformly, whereby a good measurement result was obtained. However, when the HCR was 43%, the spreading of the whole blood sample was slow and slightly non-uniform, and further, when the HCT was 51%, the spreading was poor and non-uniform.

On the other hand, when the cotton broad cloth prepared in accordance with the method of this invention (i.e., the cloth being woven by mixed cotton yarns of 65% polyethylene terephthalate and 35% cotton and being rendered hydrophilic) was used as a spreading layer of the multilayered analysis sheet, a measurement result was good even with the HCT exceeding 40%, and even at the HCT of 58%, uniform spreading was attained.

The relationship between HCT and spreading property is shown in Table 2 below.

TABLE 2

| Spreading Layer | Spreading Property Hematocrit Value | | | | | |
|---|---|---|---|---|---|---|
| | 24% | 31% | 43% | 51% | 58% | 66% |
| A (Example 5) | good | good | good | good | good | fair |
| B (Comparative Example 2) | good | good | fair | fair | poor | poor |

A: Composed of cloth woven by mixed cotton yarns of 65% polyethylene terephthalate and 35% cotton
B: Composed of 100% cotton In the evaluation shown in Table 2, "good" means that the sample was uniformly spread; "fair" means that the sample was slowly and slightly non-uniformly spread; and "poor" means that the sample was non-uniformly spread, respectively.

EXAMPLE 6

Using a multilayered analysis sheet for quantitative analysis of glucose comprising a liquid sample-spreading layer of a cotton broad cloth woven by mixed cotton yarns of 65% polyethylene terephthlate and 35% cotton as prepared in the same manner as in Example 1, a coloration ability was evaluated with respect to whole blood samples having various HCT's.

As the result, it was found that at a region around a glucose concentration in blood of 70 mg/dl, only a change of about ±9% was given in a range of HCT of from 20% to 70%, and at a region around a glucose concentration in blood of 200 mg/dl, only a change of about ±2.8% was given in the same range of HCT.

EXAMPLE 7 AND COMPARATIVE EXAMPLE 3

Figure 3:
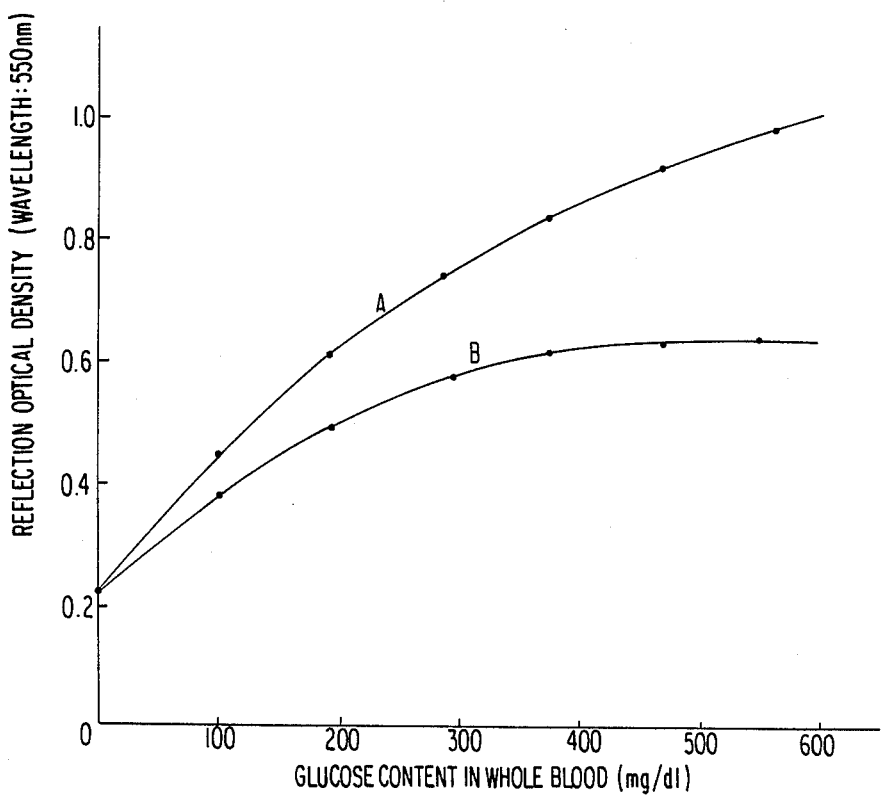
FIG. 3 is a graph showing the relationship between glucose content in whole blood and reflection optical density using the multilayered analysis sheets as obtained in Example 7 and Comparative Example 3, where a curve A means a case that a cotton broad cloth woven by mixed cotton yarns of 65% polyethylene terephthalate and 35% cotton was used as a spreading layer (Example 7), and a curve B means a case that a cotton broad cloth of 100% cotton was used as a spreading layer (Comparative Example 3).

In the same manner as in Example 5, a fresh blood was taken from a healthy human vein, to which a glucose powder was then added, to prepare whole blood samples having various glucose concentrations. The samples were incubated at room temperature for 6 minutes, and the reflection optical density at a wavelength of 550 nm was measured. The relationship between the glucose concentration in whole blood and the reflection optical density is shown in FIG. 3.

When the spreading layer composed of 100% cotton cloth (Comparative Example 3) is concerned, where the glucose concentration exceeds 400 mg/dl, coloration ability was controlled, whereby quantitative property was lost. On the other hand, when the spreading layer composed of a cotton broad cloth woven by mixed cotton yarns of 65% polyethylene terephthalate and 35% cotton (Example 7) is concerned, even when the glucose concentration is 600 mg/dl, spreading property was good, and coloration ability was maintained as well as quantitative property was good.

While the invention has been described in detail and with reference to specific embodiments thereof, it will be apparent to one skilled in the art that various changes and modifications can be made therein without departing from the spirit and scope thereof.

What is claimed is:

1. An analysis material sheet, comprising:
   a water-impermeable support; and
   a fabric layer comprising a fabric including about 10% or more of a polyethyleneterephthalate synthetic hydrophobic organic polymer fiber and the remainder being natural fiber provided on said support, said fabric layer containing a reagent and being physically activated on at least one surface thereof to render the fabric layer hydrophilic and provide increased adhesiveness, with said physically activated surface being adhered to said support to form an integral structure, wherein said physical activation is conducted by a treatment selected from the group consisting of a glow discharge treatment, plasma discharge and a corona discharge treatment.

2. An analysis material sheet as claimed in claim 1, wherein an adhesive layer is provided between said support and said fabric layer.

3. An analysis material sheet as claimed in claim 1, wherein said fabric layer comprises about 30% or more of said hydrophobic organic polymer fiber.

4. An analysis material sheet as claimed in claim 1, wherein said natural fiber is fiber selected from the group consisting of cotton, kopak, flax, hemp, ramie and silk.

5. An analysis material sheet as claimed in claim 1, wherein the fabric layer comprises 100% of said hydrophobic organic polymer fiber.

6. An analysis material sheet as claimed in claim 1, wherein said fabric layer comprises mixed yarns.

7. An analysis material sheet, comprising:
a reagent layer containing a reagent and having provided thereon a liquid sample-spreading layer of fabric, said fabric layer comprising a fabric including about 10% or more of a polyethyleneterephthalate synthetic hydrophobic organic polymer fiber and the remainder being natural fiber, and being physically activated on at least one surface thereof to render the fabric layer hydrophilic and provide increased adhesiveness, with said physically activated surface being adhered to said reagent layer to form an integral structure, wherein said physical activation is conducted by a treatment selected from the group consisting of a glow discharge treatment, plasma discharge treatment and a corona discharge treatment.

8. An analysis material sheet as claimed in claim 7, wherein an adhesive layer is provided between said reagent layer and said fabric layer.

9. An analysis material sheet as claimed in claim 7, wherein said fabric layer comprises about 30% or more of said hydrophobic organic polymer fiber.

10. An analysis material sheet as claimed in claim 7, wherein said natural fiber is fiber selected from the group consisting of cotton, kopak, flax, hemp, ramie and silk.

11. An analysis material sheet as claimed in claim 7, wherein the fabric layer comprises 100% of said hydrophobic organic polymer fiber.

12. An analysis material sheet as claimed in claim 7, wherein said fabric layer comprises mixed yarns.

13. An analysis material sheet as claimed in claim 1, wherein said fabric layer is provided directly on said water-impermeable support.

14. An analysis material sheet as claimed in any of claims 1 or 13, wherein said fabric layer is physically activated on both surfaces.

15. An analysis material sheet as claimed in claim 7, wherein said reagent layer is provided directly on said layer of fabric.

16. An analysis material sheet as claimed in any of claims 7 or 15, wherein said layer of fabric is physically activated on both surfaces.

17. An analysis material sheet as claimed in any of claims 1 or 15, wherein said reagent layer is water-permeable and has a transparent, water-impermeable support provided on a side opposite said spreading layer.

18. An analysis material sheet as claimed in any of claims 1 or 7, wherein the physical activation is a plasma discharge treatment.

19. An analysis material sheet as claimed in any of claims 1 or 5, wherein the physical activation is a corona discharge treatment.

20. An analysis material sheet as claimed in any of claims 1 or 7, wherein the physical activation is a glow discharge treatment.

21. An analysis material as claimed in claim 20, wherein the synthetic hydrophobic organic polymer fiber comprises 30% or more of the fabric layer.

22. An analysis material sheet as claimed in claim 21, wherein the synthetic hydrophobic organic polymer fiber comprises 100% of the fabric layer.

* * * * *